United States Patent [19]
Imperato

[11] Patent Number: 5,935,980
[45] Date of Patent: Aug. 10, 1999

[54] USE OF PYRROLIDINE DERIVATIVES IN THE TREATMENT OF ALCOHOLISM

[75] Inventor: Assunta Imperato, Paris, France

[73] Assignee: Rhône-Poulenc Rorer S.A., Antony Cédex, France

[21] Appl. No.: 08/952,937

[22] PCT Filed: May 29, 1996

[86] PCT No.: PCT/FR96/00801

§ 371 Date: Nov. 26, 1997

§ 102(e) Date: Nov. 26, 1997

[87] PCT Pub. No.: WO96/38139

PCT Pub. Date: Dec. 5, 1996

[30] Foreign Application Priority Data

Jun. 1, 1995 [FR] France .................................. 95-06530

[51] Int. Cl.$^6$ ...................... A61K 31/445; A61K 31/425; A61K 31/40
[52] U.S. Cl. ........................ 514/365; 514/317; 514/323; 514/324; 514/326; 514/422; 514/424; 514/429; 514/811
[58] Field of Search ..................... 514/317, 323, 514/324, 326, 365, 422, 424, 429, 811

[56] References Cited

U.S. PATENT DOCUMENTS 5,451,582  9/1995  Chambers et al. ...................... 514/221

FOREIGN PATENT DOCUMENTS

WO 9301167  1/1993  WIPO .
WO 94/15915  7/1994  WIPO .

OTHER PUBLICATIONS

Derwent Abstract of WO 9415915, (1994).

Derwent Abstract of WO 9301167, (1993).

*Primary Examiner*—Kimberly Jordan
*Attorney, Agent, or Firm*—Finnegan, Henderson, Farabow, Garrett & Dunner, L.L.P.

[57] ABSTRACT

The use of pyrrolidine derivatives of general formula (I) for treating chronic alcoholism or conditions caused by alcohol abuse is described.

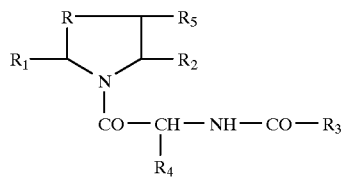

(I)

4 Claims, No Drawings

USE OF PYRROLIDINE DERIVATIVES IN THE TREATMENT OF ALCOHOLISM

This application is a 371 of PCT/FR96/00801, filed May 29, 1996.

The present invention relates to the use of derivatives of formula:

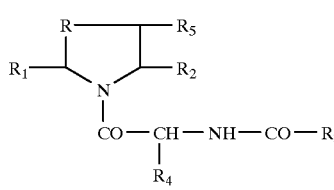

their racemates and enantiomers, when they contain one or a number of asymmetric centres, and their salts in the treatment of chronic alcoholism or of conditions due to alcohol abuse and to the application of these derivatives in the preparation of medicaments intended for the treatment of chronic alcoholism or of conditions due to alcohol abuse.

In the formula (I), either R represents a methylene, ethylene, SO, $SO_2$, or CHOH radical or a sulphur atom, $R_1$ represents a pyridyl radical which is optionally substituted by one or a number of alkyl radicals, a furyl radical which is optionally substituted by one or a number of alkyl radicals, a thienyl radical which is optionally substituted by one or a number of alkyl radicals, a quinolyl radical which is optionally substituted by one or a number of alkyl radicals, a naphthyl radical which is optionally substituted by one or a number of alkyl radicals, an indolyl radical which is optionally substituted by one or a number of alkyl radicals or a phenyl radical which is optionally substituted by one or a number of substituents chosen from halogen atoms and alkyl, alkoxy, hydroxyl, nitro, amino, monoalkylamino, dialkylamino, alkoxycarbonyl, —CO—$NR_7R_8$, —NH—CO—$CH_3$, trifluoromethyl or trifluoromethoxy radicals and $R_5$ represents a hydrogen atom, or R represents a methylene radical, $R_1$ represents a hydrogen atom and $R_5$ represents a phenyl radical, or R represents a $CHR_6$ radical and $R_1$ and $R_5$ each represent a hydrogen atom, $R_2$ represents an alkoxycarbonyl, cycloalkyloxycarbonyl, cycloalkylalkyloxycarbonyl, —$CONR_9R_{10}$ or phenyl radical which is optionally substituted by one or a number of substituents chosen from alkyl, alkoxy or hydroxyl radicals, $R_3$ represents a phenyl radical (optionally substituted by one or a number of substituents chosen from halogen atoms and alkyl, alkoxy and alkylthio radicals), a naphthyl radical, an indolyl radical, a quinolyl radical or a phenylamino radical in which the phenyl ring is optionally substituted by one or a number of substituents chosen from halogen atoms and alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyaminocarbonyl, alkoxyaminocarbonyl, tetrazol-5-yl, tetrazol-5-ylalkyl, trifluoromethylsulphonamido, alkylsulphinyl, mono- or polyhydroxyalkyl, sulpho, -alk-O—CO-alk, -alk-COOX, -alk-O-alk, -alk'-COOX, —O-alk-COOX, —CH=CH—COOX, —CO—COOX, -alk-$SO_3H$ in the salt form, —CH=CH-alk', —C(=NOH)—COOX, —S-alk-COOX, —O—$CH_2$-alk'-COOX, —CX=N—O-alk-COOX, -alk-N(OH)—CO-alk or 2,2-dimethyl-4,6-dioxo-1,3-dioxan-5-yl radicals, $R_4$ represents a hydrogen atom or an alkyl radical, $R_6$ represents a phenyl radical, $R_7$ represents a hydrogen atom or an alkyl, phenylalkyl or phenyl radical which is optionally substituted by one or a number of substituents chosen from halogen atoms and alkyl, alkoxy and alkylthio radicals, $R_8$ represents an alkyl, phenylalkyl or phenyl radical which is optionally substituted by one or a number of substituents chosen from halogen atoms and alkyl, alkoxy and alkylthio radicals, or else $R_7$ and $R_8$ form, with the nitrogen atom to which they are attached, a saturated or unsaturated, mono- or polycyclic heterocycle containing 4 to 9 carbon atoms and one or a number of heteroatoms (O, N) and which is optionally substituted by one or a number of alkyl radicals, $R_9$ represents a hydrogen atom or an alkyl, cycloalkylalkyl, cycloalkyl, phenylalkyl or phenyl radical which is optionally substituted by one or a number of substituents chosen from halogen atoms and alkyl, alkoxy and alkylthio radicals, $R_{10}$ represents an alkyl, cycloalkylalkyl, cycloalkyl, phenylalkyl or phenyl radical which is optionally substituted by one or a number of substituents chosen from halogen atoms and alkyl, alkoxy and alkylthio radicals, or else $R_9$ and $R_{10}$ form, together with the nitrogen atom to which they are attached, a saturated or unsaturated, mono- or polycyclic heterocycle containing 4 to 9 carbon atoms and one or a number of heteroatoms (O, N, S) and which is optionally substituted by one or a number of alkyl radicals, X represents a hydrogen atom or an alkyl or phenylalkyl radical, alk represents an alkyl or alkylene radical, alk' represents a hydroxyalkyl, hydroxyalkylene, alkoxyalkyl or alkoxyalkylene radical.

In the preceding definitions and those which will be mentioned below, except when otherwise mentioned, the alkyl, alkylene and alkoxy radicals and the alkyl, alkylene and alkoxy portions contain 1 to 4 straight- or branched-chain carbon atoms, the acyl radicals or portions contain 2 to 4 carbon atoms and the cycloalkyl radicals and portions contain 3 to 6 carbon atoms.

When $R_7$ and $R_8$ form, with the nitrogen atom to which they are attached, a heterocycle, the latter is preferably a piperidino ring, which is optionally substituted by one or a number of alkyl radicals, or a 1,2,3,4-tetrahydroquinoline ring.

When $R_9$ and $R_{10}$ form, with the nitrogen atom to which they are attached, a heterocycle, the latter is preferably a piperidino, 1-perhydroazepinyl, 1,2,3,6-tetrahydro-1-pyridyl, 1,2,3,4-tetrahydro-1-quinolyl, 1-pyrrolidinyl, 1,2,3,4-tetrahydro-2-isoquinolyl, thiomorpholino or 1-indolyl ring, it being possible for these rings optionally to be substituted by at least one alkyl radical.

The compounds of formula (I) containing one or a number of asymmetric centres exhibit isomer forms. The racemates and the enantiomers of these compounds also form part of the invention.

The compounds of formula (I) can optionally exist in the form of addition salts with an inorganic or organic acid.

The compounds of formula (I) containing a carboxyl, sulpho or alk-$SO_3H$ residue can also exist in the form of metal salts or of addition salts with pharmaceutically acceptable nitrogenous bases.

Mention may be made, as examples of pharmaceutically acceptable salts, of the addition salts with inorganic or organic acids (such as acetate, propionate, succinate, benzoate, fumarate, maleate, oxalate, methanesulphonate, isethionate, theophyllinacetate, salicylate, methylenebis(β-oxynaphthoate), hydrochloride, sulphate, nitrate and phosphate), the salts with alkali metals (sodium, potassium, lithium) or with alkaline-earth metals (calcium, magnesium), the ammonium salt or the salts of nitrogenous bases (ethanolamine, trimethylamine, methylamine, benzylamine, N-benzyl-β-phenethylamine, choline, arginine, leucine, lysine or N-methylglucamine).

The products of formula (I) and their salts can be prepared under the conditions described in International Application PCT WO 93/01167.

From International Application PCT WO 93/01167, the compounds of formula (I) have advantageous pharmacological properties. These compounds have a strong affinity for cholecystokinin (CCK) and gastrin receptors and are thus useful in the treatment and prevention of disorders linked to CCK and to gastrin in the nervous system and the gastrointestinal system.

Thus, according to International Application PCT WO 93/01167, the compounds can be used for the treatment or the prevention or psychoses, of anxious disorders, of Parkinsons disease, of tardive dyskinesia, of irritable bowel syndrome, of acute pancreatitis, of ulcers, of disorders of intestinal motility or of certain tumours sensitive to CCK and as an appetite regulator. These compounds, which also have a potentiating effect on the analgesic activity of narcotic and non-narcotic medicaments, can have an appropriate analgesic effect. Moreover, the compounds which have a strong affinity for CCK receptors modify memorising abilities, can be effective in memory disorders.

It has now been found that the compounds of formula (I), their racemates and enantiomers, when they contain at least one asymmetric centre, and their salts are particularly useful for the treatment of chronic alcoholism or of conditions resulting from alcohol abuse.

By taking the work by H. H. Samson and R. A. Harris, Trends Pharmacol. Sci., 13, 206–211 (1992) as the basis and by carrying out tests on rats trained to a high alcohol consumption, the effectiveness of the compounds according to the invention can be shown by noting the behaviour of rats with respect to the consumption of alcohol. On carrying out repeat treatments with the products according to the invention at doses of between 5 and 25 mg/kg i.p. per day for 14 days, the alcohol consumption of the animals treated decreases by $\frac{2}{3}$.

In rats which have been made alcohol dependent, the compounds make possible a decrease in alcohol consumption which can reach more than 40% when the compounds according to the invention are administered at doses of between 5 and 50 mg/kg intraperitoneally.

The activity of the products can also be demonstrated in monkeys living in the Caribbean Islands (*Cercopithecus aethiops*), some of which voluntarily consume alcoholic drinks. When the compounds according to the invention are administered at doses of between 4 and 50 mg/kg orally for 2 weeks to monkeys accustomed to consuming more than 5 g of ethanol per day, the consumption decreases by 40% in the first week and by 30% in the second. Moreover, the products according to the invention do not influence the consumption of food, since the average weight remains constant, or the consumption of water.

The compounds of formula (I) for which R represents a methylene radical, a sulphur atom or an SO radical, $R_1$ represents an optionally substituted phenyl radical, $R_2$ represents a phenyl or alkoxycarbonyl radical, $R_4$ and $R_5$ represents a hydrogen atom and $R_3$ represents a phenylamino radical in which the phenyl ring is substituted by a carboxyl, -alk-COOH, —S-alk-COOH, hydroxyalkyl, alk'-COOH or alkSO₃H, or hydroxyiminoalkyl radical are particularly advantageous. The products of formula (I) in which $R_1$ and $R_2$ are in the cis position with respect to one another are more particularly advantageous.

The following compounds and their salts are particularly advantageous:

tert-butyl (2RS,5SR)-1-{2-[3-(3-(RS)-1-hydroxyethyl)-phenyl)ureido]acetyl}-5-phenylprolinate, 2-{3-{3-[2-(2S,5R)-2-tert-butoxycarbonyl-5-phenyl-1-pyrrolidinyl)-2-oxoethyl]ureido}phenyl}propionic acid (2RS,5SR)-{3-{3-[2-(2-tert-butoxycarbonyl-5-phenyl-1-pyrrolidinyl)-2-oxoethyl]ureido}phenylthio}acetic acid, (2R,4R)-3-{3-[2-(4-tert-butoxycarbonyl-(2-fluoro-3-thiazolidinyl)-2-oxoethyl]ureido}phenylacetic acid, 2-{3-{3-[2-((2R,4R)-4-tert-butoxycarbonyl-2-(2-fluorophenyl)-3-thiazolidinyl)-2-oxoethyl]ureido}-phenyl}propionic acid, potassium (RS)-1-{3-{3-[2-((2R,4R)-4-tert-butoxycarbonyl-2-phenyl-3-thiazolidinyl))-2-oxoethyl]ureido}phenyl}ethanesulphonate, potassium (RS)-1-{3-{3-[2-((2S,5R)-2-tert-butoxycarbonyl-5-phenyl-1-pyrrolidinyl)-2-oxoethyl]ureido}phenyl}ethanesulphonate, potassium (2S,5R)-1-{3-{3-[2-(2-tert-butoxycarbonyl-5-phenyl-1-pyrrolidinyl)-2-oxoethyl]ureido}phenyl-methanesulphonate, (2S,5R)-3-{3-[2-2-tert-butoxycarbonyl-5-phenyl-1-pyrrolidinyl)-2-oxoethyl]ureido}benzoic acid, (2RS,5SR)-3-{3-{2-[2-tert-butoxycarbonyl-5-(2-fluorophenyl)-1-pyrrolidinyl]-2-oxoethyl}ureido}benzoic acid, (cis)-3-{3-[2-(2,5-diphenyl-1-pyrrolidinyl)-2-oxoethyl]ureido}benzoic acid, (2RS,5SR)-3-{{2-[2-(2-hydroxyphenyl)-5-phenyl-1-pyrrolidinyl]-2-oxoureido}phenylacetic acid, (2R,4R)-3-{3-[2-(4-tert-butoxycarbonyl-2-phenyl-3-thiazolidinyl)-2-oxoethyl]ureido}phenylacetic acid, (2R,4R)-3-{3-[2-(4-tert-butoxycarbonyl-2-phenyl-3-thiazolidinyl)-2-oxoethyl]ureido}benzoic acid, 2-{3-{3-[2-((1RS,2R,4R)-4-tert-butoxycarbonyl-2-(2-fluorophenyl)-1-oxide-3-thiazolidinyl)-2-oxoethyl}-ureido}phenyl}propionic acid, (2R,4R)-3-{3-[2-(4-tert-butoxycarbonyl-2-(2,3-difluorophenyl)-3-thiazolidinyl)-2-oxoethyl]ureido}phenylacetic acid, tert-butyl (2RS,5SR)-1-{2-{3-[(E)-3-(1-(hydroxyimino)ethyl)phenyl]ureido}acetyl}-5-phenylprolinate.

The medicaments according to the invention consist of a compound of formula (I) in the free form or in the form of an addition salt with a pharmaceutically acceptable acid, in the pure state or in the form of a composition in which it is combined with any other pharmaceutically compatible product, which can be inert or physiologically active. The medicaments according to the invention can be used orally, parenterally, rectally or topically.

Tablets, pills, powders (gelatin capsules or cachets), or granules can be used as solid compositions for oral administration. In these compositions, the active principle according to the invention is mixed with one or a number of inert diluents, such as starch, cellulose, sucrose, lactose or silica, under an argon stream. These compositions can also comprise substances other than the diluents, for example one or a number of lubricating agents such as magnesium stearate or talc, a colouring agent, a coating agent (dragées) or a varnish.

Pharmaceutically acceptable solutions, suspensions, emulsions, syrups and elixirs containing inert diluents such as water, ethanol, glycerol, vegetable oils or paraffin oil can be used as liquid compositions for oral administration. These compositions can comprise substances other than the diluents, for example wetting, sweetening, thickening, flavouring or stabilizing substances.

The sterile compositions for parenteral administration can preferably be aqueous solutions or non-aqueous solutions, suspensions or emulsions. Water, propylene glycol, a polyethylene glycol, vegetable oils, in particular olive oil, injectable organic esters, for example ethyl oleate, or other suitable organic solvents can be used as solvent or vehicle. These compositions can also contain adjuvants, in particular wetting, isotonizing, emulsifying, dispersing and stabilizing agents. Sterilization can be carried out in several ways, for example by aseptic filtration, by incorporating sterilizing agents in the composition, by irradiation or by heating. They can also be prepared in the form of sterile solid compositions which can be dissolved at the time of use in sterile water or any other injectable sterile medium.

The compositions for rectal administration are suppositories or rectal capsules which contain, besides the active product, excipients such as cocoa butter, semi-synthetic glycerides or poly(ethylene glycol)s.

The compositions for topical administration can be, for example, creams, lotions, eye drops, mouthwashes, nose drops or aerosols.

In human therapeutics, the medicaments according to the invention are particularly useful in the treatment of chronic alcoholism and of conditions due to alcohol abuse.

The doses depend on the desired effect, on the duration of treatment and on the administration route used; they are generally between 0.05 g and 1 g per day orally for an adult with unit doses ranging from 10 mg to 500 mg of active substance.

Generally, the doctor will determine the appropriate dosage depending on the age, weight and all the other factors specific to the subject to be treated.

The following examples illustrate medicaments according to the invention:

EXAMPLE A

Gelatin capsules containing 50 mg of active product are prepared, according to the usual technique, which have the following composition:

Compound of formula (I) 50 mg
Cellulose 18 mg
Lactose 55 mg
Colloidal silica 1 mg
Sodium carboxymethylstarch 10 mg
Talc 10 mg
Magnesium stearate 1 mg

EXAMPLE B

Tablets containing 50 mg of active product are prepared, according to the usual technique, which have the following composition:

Compound of formula (I) 50 mg
Lactose 104 mg
Cellulose 40 mg
Polyvidone 10 mg
Sodium carboxymethylstarch 22 mg
Talc 10 mg
Magnesium stearate 2 mg
Colloidal silica 2 mg Mixture of hydroxymethylcellulose, glycerol and titanium oxide (72/3.5/24.5) q.s. for one coated tablet completed to 245 mg

EXAMPLE C

An injectable solution containing 10 mg of active product is prepared which has the following composition:

Compound of formula (I) 10 mg
Benzoic acid 80 mg
Benzyl alcohol 0.06 cm$^3$
Sodium benzoate 80 mg
95% ethanol 0.4 cm$^3$
Sodium hydroxide 24 mg
Propylene glycol 1.6 cm$^3$
Water q.s. for 4 cm$^3$

I claim:

1. A method which allows a patient of his own accord to reduce his consumption of alcohol, which comprises administering to the patient a pharmaceutical composition which comprises a compound of the formula I

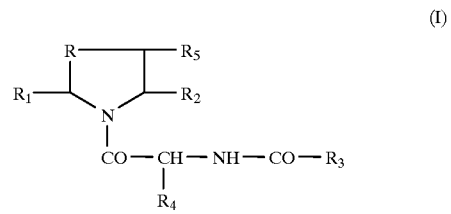

wherein

R represents a methylene, ethylene, SO, SO$_2$, or CHOH radical or a sulphur atom, R$_1$ represents a pyridyl radical which is unsubstituted or substituted by one or a number of alkyl radicals, a furyl radical which is unsubstituted or substituted by one or a number of alkyl radicals, a thienyl radical which is unsubstituted or substituted by one or a number of alkyl radicals, a quinolyl radical which is unsubstituted or substituted by one or a number of alkyl radicals, a naphthyl radical which is unsubstituted or substituted by one or a number of alkyl radicals, an indolyl radical which is unsubstituted or substituted by one or a number of alkyl radicals or a phenyl radical which is unsubstituted or substituted by one or a number of substituents which represent halogen atoms or alkyl, alkoxy, hydroxyl, nitro, amino, monoalkylamino, dialkylamino, alkoxycarbonyl, —CO—NR$_7$R$_8$, —NH—CO—CH$_3$, trifluoromethyl or trifluoromethoxy radicals and R$_5$ represents a hydrogen atom, or R represents a methylene radical, R$_1$ represents a hydrogen atom and R$_5$ represents a phenyl radical, or R represents a CHR$_6$ radical and R$_1$ and R$_5$ each represent a hydrogen atom, R$_2$ represents an alkoxycarbonyl, cycloalkyloxycarbonyl, cycloalkylalkyloxycarbonyl, —CONR$_9$R$_{10}$ or phenyl radical which is unsubstituted or substituted by one or a number of substituents which represent alkyl, alkoxy or hydroxyl radicals, R$_3$ represents a phenyl radical, unsubstituted or substituted by one or a number of substituents which represent halogen atoms or alkyl, alkoxy or alkylthio radicals, or R$_3$ represents a naphthyl radical, an indolyl radical, a quinolyl radical or a phenylamino radical in which the phenyl ring is unsubstituted or substituted by one or a number of substituents which represent halogen atoms or alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyaminocarbonyl, alkoxyaminocarbonyl, tetrazol-5-yl, tetrazol-5-ylalkyl, trifluoromethylsulphonamido, alkylsulphinyl, mono- or polyhydroxyalkyl, sulpho, -alk-O—CO-alk, -alk-COOX, -alk-O-alk, -alk'-COOX, —O-alk-COOX, —CH=CH—COOX, —CO—COOX, -alk-$SO_3$H in the salt form, —CH=CH-alk', —C(=NOH)—COOX, —S-alk-COOX, —O—$CH_2$-alk'-COOX, —CX=N—O-alk-COOX, -alk-N(OH)—CO-alk or 2,2-dimethyl-4,6-dioxo-1,3-dioxan-5-yl radicals, $R_4$ represents a hydrogen atom or an alkyl radical, $R_6$ represents a phenyl radical, $R_7$ represents a hydrogen atom or an alkyl, phenylalkyl or phenyl radical which is unsubstituted or substituted by one or a number of substituents which represent halogen atoms or alkyl, alkoxy or alkylthio radicals, $R_8$ represents an alkyl, phenylalkyl or phenyl radical which is unsubstituted or substituted by one or a number of substituents which represent halogen atoms or alkyl, alkoxy or alkylthio radicals, or $R_7$ and $R_8$ form, together with the nitrogen atom to which they are attached, a saturated or unsaturated, mono- or polycyclic heterocycle containing 4 to 9 carbon atoms and one or a number of heteroatoms, O or N, and which heterocycle is unsubstituted or substituted by one or a number of alkyl radicals, $R_9$ represents a hydrogen atom or an alkyl, cycloalkylalkyl, cycloalkyl, phenylalkyl or phenyl radical which is unsubstituted or substituted by one or a number of substituents which represent halogen atoms or alkyl, alkoxy or alkylthio radicals, $R_{10}$ represents an alkyl, cycloalkylalkyl, cycloalkyl, phenylalkyl or phenyl radical which is unsubstituted or substituted by one or a number of substituents which represent halogen atoms or alkyl, alkoxy or alkylthio radicals. or $R_9$ and $R_{10}$ form, together with the nitrogen atom to which they are attached, a saturated or unsaturated, mono- or polycyclic heterocycle containing 4 to 9 carbon atoms and one or a number of heteroatoms, O, N or S, and which heterocycle is unsubstituted or substituted by one or a number of alkyl radicals, X represents a hydrogen atom or an alkyl or phenylalkyl radical, alk represents an alkyl or alkylene radical, and alk' represents a hydroxyalkyl, hydroxyalkylene, alkoxyalkyl or alkoxyalkylene radical, it being understood that the alkyl, alkylene and alkoxy radicals and the alkyl, alkylene and alkoxy portions contain 1 to 4 straight- or branched-chain carbon atoms, the acyl radicals and portions contain 2 to 4 carbon atoms and the cycloalkyl radicals and portions contain 3 to 6 carbon atoms, or an addition salt of the compound of the formula I with a pharmaceutically acceptable acid, or a racemate or enantiomer of the compound of the formula I, when the compound contains at least one asymmetric center, said pharmaceutical composition also comprising a pharmaceutically acceptable carrier.

2. A method as claimed in claim 1, wherein R of formula I represents a methylene radical, a sulphur atom or an SO radical, $R_1$ represents an unsubstituted or substituted phenyl radical, $R_2$ represents a phenyl or alkoxy carbonyl radical, $R_4$ and $R_5$ represent a hydrogen atom and $R_3$ represents a phenylamino radical in which the phenyl ring is substituted by a carboxyl, -alk-COOH, —S-alk-COOH, hydroxyalkyl, alk'-COOH or alk-$SO_3$H radical in the salt form.

3. A method as claimed in claim 1, wherein the compound of the formula I is selected from the following compounds:

tert-butyl (2RS,5SR)-1-{2-[3-(3-(RS)-1-hydroxyethyl)phenyl)ureido]acetyl}-5-phenylprolinate, 2-{3-{3-[2-((2S,5R)-2-tert-butoxycarbonyl-5-phenyl-1-pyrrolidinyl)-2-oxoethyl]ureido}-phenyl}propionic acid, (2RS,5SR)-{3-{3-[2-(2-tert-butoxycarbonyl-5-phenyl-1-pyrrolidinyl)-2-oxoethyl]ureido}-phenylthio}acetic acid, (2R,4R)-3-{3-[2-(4-tert-butoxycarbonyl-(2-fluoro-3-thiazolidinyl)-2-oxoethyl]ureido}-phenylacetic acid, 2-{3-{3-[2-((2R,4R)-4-tert-butoxycarbonyl-2-(2-fluorophenyl)-3-thiazolidinyl)-2-oxoethyl]ureido}phenyl}propionic acid, potassium (RS)-1-{3-{3-[2-((2R,4R)-4-tert-butoxycarbonyl-2-phenyl-3-thiazolidinyl))-2-oxoethyl]ureido}phenyl}ethanesulphonate, potassium (RS)-1-{3-{3-[2-((2S,5R)-2-tert-butoxycarbonyl-5-phenyl-1-pyrrolidinyl)-2-oxoethyl]ureido}phenyl}ethanesulphonate, potassium (2S,5R)-1-{3-{3-[2-(2-tert-butoxycarbonyl-5-phenyl-1-pyrrolidinyl)-2-oxoethyl]ureido}phenylmethanesulphonate, (2S,5R)-3-{3-[2-2-tert-butoxycarbonyl-5-phenyl-1-pyrrolidinyl)-2-oxoethyl]ureido}benzoic acid, (2RS,5SR)-3-{3-{2-[2-tert-butoxycarbonyl-5-(2-fluorophenyl)-1-pyrrolidinyl]-2-oxoethyl}ureido}benzoic acid, -(cis)-3-{3-[2-(2,5-diphenyl-1-pyrrolidinyl)-2-oxoethyl]-ureido}benzoic acid, (2RS,5SR)-3-{{2-[2-(2-hydroxyphenyl)-5-phenyl-1-pyrrolidinyl]-2-oxoureido}phenylacetic acid, (2R,4R)-3-{3-[2-(4-tert-butoxycarbonyl-2-phenyl-3-thiazolidinyl)-2-oxoethyl]ureido}phenylacetic acid, (2R,4R)-3-{3-[2-(4-tert-butoxycarbonyl-2-phenyl-3-thiazolidinyl)-2-oxoethyl]ureido}benzoic acid, 2-{3-{3-[2-((1RS,2R,4R)-4-tert-butoxycarbonyl-2-(2-fluorophenyl)-1-oxide-3-thiazolidinyl)-2-oxoethyl}ureido}phenyl}propionic acid, (2R,4R)-3-{3-[2-(4-tert-butoxycarbonyl-2-(2,3-difluorophenyl)-3-thiazolidinyl)-2-oxoethyl]ureido}phenylacetic acid, and tert-butyl (2RS,5SR)-1-{2-{3-[(E)-3-(1-(hydroxyimino)ethyl)phenyl]ureido}acetyl}-5-phenylprolinate.

4. A method as claimed in claim 1, wherein the compound of the formula I is 2-{3-{3-[2-((2R,4R)-4-tert-butoxycarbonyl-2-(2-fluorophenyl)-3-thiazolidinyl)-2-oxoethyl]ureido}phenyl}propionic acid.

* * * * *